United States Patent [19]

Chan

[11] Patent Number: 4,666,862

[45] Date of Patent: May 19, 1987

[54] FLUORESCENT ENERGY TRANSFER WITH PHYCOBILIPROTEINS

[75] Inventor: Joseph L. W. Chan, Quincy, Mass.

[73] Assignee: Ortho Diagnostic Systems Inc., Raritan, N.J.

[21] Appl. No.: 640,499

[22] Filed: Aug. 14, 1984

[51] Int. Cl.[4] ............... G01N 33/566; G01N 33/536; G01N 33/542
[52] U.S. Cl. .................................... 436/501; 436/800; 436/536; 436/537; 436/546; 530/370
[58] Field of Search ............... 436/536, 501, 537, 546, 436/800, 816; 252/301.16; 424/11; 530/370

[56] References Cited

U.S. PATENT DOCUMENTS

| | | | |
|---|---|---|---|
| 3,996,345 | 12/1976 | Ullman | 436/537 |
| 4,166,105 | 8/1979 | Hirschfeld | 436/536 |
| 4,174,384 | 11/1979 | Ullman | 436/537 |
| 4,199,559 | 4/1980 | Ullman | 436/537 |
| 4,261,968 | 4/1981 | Ullman | 436/546 |
| 4,542,104 | 9/1985 | Stryer | 436/536 |

FOREIGN PATENT DOCUMENTS 0076695 4/1983 European Pat. Off. .
0075982 4/1983 European Pat. Off. .

OTHER PUBLICATIONS

Wingender, E., *Anal. Biochem.*, vol. 121, 1982, pp. 146–150.
Hardy, R. R., et al, *Nature*, vol. 306, 1983, pp. 270–272.
Muirhead, K. A., et al, *Bio/Technology*, vol. 3, 1985, pp. 337–356.
Sahlin, S., et al, *J. Immunol. Meth.*, vol. 60, 1983, pp. 115–124.

*Primary Examiner*—Esther M. Kepplinger
*Assistant Examiner*—Jeremy Jay
*Attorney, Agent, or Firm*—Mark A. Hofer

[57] ABSTRACT

Dyes are provided comprising phycobiliproteins having covalently coupled thereto a plurality of small molecular weight organic dyes under conditions permitting energy transfer mechanisms to operate therebetween. The resultant label may then be used in virtually any immunoassay format.

2 Claims, No Drawings

FLUORESCENT ENERGY TRANSFER WITH PHYCOBILIPROTEINS

FIELD OF THE INVENTION

This invention relates generally to detectable labels useful in immunoassay methods for detecting soluble substances or analytes such as antigens and more specifically, relates to fluorescent labels based on energy transfer and employing phycobiliproteins.

BACKGROUND OF THE INVENTION

The detection of specified antigens (defined as a substance whose introduction into an animal stimulates the production of antibodies capable of reacting specifically therewith), haptens (a substance requiring additional accessory materials before its introduction into an animal stimulates the production of antibodies specific therefor), analytes and the like substances (hereinafter collectively referred to as ligands) in body fluids such as blood, sputum, urine, and the like has in recent years become of utmost importance in both the research and clinical environment. The detection of ligands, particularly antigens, and antibodies specific therefor can often be related to various disease states and consequently is of extreme usefulness in diagnosis as well as gaining basic understandings concerning the genesis of disease as well as monitoring the effectiveness of therapies therefor.

Consequently, improved methods for detecting ligands in aqueous samples are constantly sought. It is an object of the present invention to improve such immunoassay methods generally by providing improved and novel detectable labels for use therewith.

Immunoassays in general are based upon the immunological reaction between proteins such as antibodies, antibody fragments or even artificially generated peptides (hereinafter collectively referred to as ligand binding partners) and the substance for which they are specific, generally referred to herein as ligands. Immunological reactions are generally characterized by their high specificity and accordingly numerous schemes have been developed in order to take advantage of this characteristic. Typically, such schemes require either purified ligand to compete with the ligand being measured and a labeled and immobilized antibody or ligand binding partner, or multiple immobilized and labeled ligand binding partners reactive between themselves and the ligand. All these methods uniformly rely upon the detectability of the associated label.

Sensitivity of detection in turn is generally related to the type of label employed and the quality and type of equipment available to detect it. For instance, isotopes have traditionally been recognized as providing a high level of sensitivity since present technological capability allows for the detection of a single isotopic atom but, are nonetheless largely disfavored due to the inherent health dangers imposed by radioisotopes. Further, the procedural difficulties necessitated by careful handling and disposal of isotopic reagents have stimulated the search for better labels.

For this reason, two other types of labels have become heavily favored in recent years, to wit fluorescent molecules and enzymes. Enzymes advantageously offer a biological amplification system due to the continuous or persistant chemical activity characteristic of enzymes whereby substrate is transformed into detectable product. Thus, enzymes are, in fact, an indirect label since it is the product of enzyme activity that is detected, not the enzyme itself. Such enzyme or enzyme linked immunosorbant assays (the so-called ELISA systems), however, disadvantageously require extra steps and reagents in order to supply the substrates under conditions suitable for the conversion to, and detection of resultant product.

Fluorescent molecules, although not offering the amplification advantage of enzymes, have found favor due to the simplicity of the equipment required for their detection and associated methods generally. The fluorescent molecules need merely be illuminated at an appropriate frequency and the resultant spectral emissions detected by photodetectors or the like having sensitivity in the appropriate emission spectral region.

Indeed, numerous instruments including for instance the Ortho Spectrum III TM (available from the assignee hereof) employ fluorescently labeled antibodies to detect the presence of antigenic markers on cells which are hydrodynamically focused to pass single file, through an illumination zone. Spectrally specific illumination is advantageously provided by a laser and fluorescent emission detected by photodetectors arranged at suitable locations. In fact, numerous fluorescent dyes have been discovered and are commercially available offering fluorescent emissions in a variety of wavelengths.

Despite the availability of an impressive array of fluorescent dyes, there has been a relative lack of molecules which are excited and emit in the long wavelengths, i.e., the red spectrum. Such characteristics are desirable because these wavelengths can be more easily detectable to the exclusion of natural fluorescence from other biomolecules. Such natural fluorescence otherwise creates a background signal often masking the desired signal from the fluorescent label thereby lowering sensitivity.

Further, most fluorescent molecules typically have an emission spectra closer to the ultraviolet range thereby necessitating relatively expensive light sources such as argon lasers and the like. As may be readily appreciated, any added complexity and price of instrumentation reduces their availability to clinical laboratories and hospitals, particularly in light of recent financial pressures imposed by DRG (Diagnosis Related Group) regulations and the like.

Thus, it is an object of the present invention to provide fluorescent labels which can be excited by relatively inexpensive light sources such as helium neon lasers.

Oi et al., in an article entitled "Fluorescent Phycobiliprotein Conjugates For Analyis of Cells and Molecules", The Journal of Cell Biology, 93:981-986 (1982), described the synthesis of a new class of dyes having fluorescence emissions in the orange-red spectral region. These fluorescent molecules, or phycobiliproteins, are derived from various species of algae. Such phycobiliproteins advantageously exhibit comparatively high efficiency at wavelengths in the neighborhood of those desired.

Fluorescence energy transfer is a process sometimes occurring between two molecules, one of which is deemed a donor and the other generally called an acceptor. Typically, the donor molecule is excited by energy of one wavelength (actually a bell-shaped spectrum of wavelengths having a peak or optimum wavelength preferably selected to be at the peak of the available illumination spectrum) and exhibits a fluorescence energy emission curve much like that of the typical fluorophore. The acceptor molecule is preferably chosen to have a suitable excitation wavelength, preferably so that a significant portion of its excitation spectrum falls within the emission wavelength spectrum of the donor molecule. Under optimum conditions the donor peak emission wavelength will be approximately equal to the acceptor peak excitation wavelength. Acceptance by the acceptor molecule of energy by energy transfer mechanisms from the donor molecule results in apparent diminished fluorescence of the donor molecule. The acceptor molecule in turn may be a chromophore, i.e., a molecule exhibiting no innate fluorescence, but will preferably be a fluorescent molecule having its own characteristic fluorescence emission spectra which increases with energy transfer.

Energy transfer in a true fluorescence energy transfer pair is believed to take place by a dipole-dipole energy transfer process the efficiency of which varies with the inverse 6th power of the distance between the donor and acceptor molecules. Thus, changes in fluorescent energy emission may be used to determine proximity relationships between acceptor and donor molecules or molecules to which they are attached. Further, the dipole-dipole energy transfer process, pursuant to Forster's theory, also has an orientation component which affects transfer efficiency. These and other fluorescence energy transfer considerations have been described in a useful reference written by Lubert Stryer entitled "Fluorescence Energy Transfer as a Spectroscopic Ruler", Annuals Review Biochem., 47:819–846 (1978).

This distance sensitive aspect of fluorescence energy transfer has been employed as a labeling technique by Ullman et al. in U.S. Pat. Nos. 4,199,559; 3,996,345; 4,174,384; and 4,261,968. Ullman teaches the employment of a fluorescer-quencher pair of molecules wherein the fluorescer molecule is excited by light of a specified wavelength and fluoresces at a longer wavelength. The presence of a non-fluorescent quencher molecule in close proximity to the fluorescer, however, results in the quenching of this fluorescence thereby contributing to an overall decrease in measurable fluorescence. Accordingly, Ullman's assays employ two different antibodies labeled with either fluorescer or quencher molecules for specific and simultaneous immunological reaction with the ligand to be detected. These methods require the ligand to be polyvalent in nature in order to provide the necessary multiple binding sites for the attachment of multiple antibodies. These methods also require the two members of the fluorescent energy pair to be part of separate reagents.

Alternately, and in the case of monovalent ligands, Ullman teaches the use of a ligand-analog, the substantial proportion of which has the same spatial and polar organization as the ligand to define one or more determinant or epitopic sites capable of competing with the ligand for the binding sites of the receptor or antibody. The ligand-analog differs from the ligand in the absence of an atom or functional group at the site of binding or in having a linking group which has been introduced in place of one or more atoms originally present in the ligand. Typically then, this ligand-analog is labeled with either the fluorescer or quencher molecule and competes with the ligand of the sample for the binding site on an antibody which is labeled with the other molecule of the fluorescer-quencher pair. In this mode, increasing concentrations of ligand may be expected to compete more effectively for the antibody binding sites thereby displacing labeled ligand-analogs and reducing the amount of fluorescent quenching they would otherwise contribute.

Ullman's assays disadvantageously require polyvalency of the ligand or analyte to be detected, or in the alternative, disadvantageously require the production of purified intact ligand-analogs to compete with the ligand. Experience has demonstrated the production of such substances is a generally disadvantageous, difficult, time consuming and expensive proposition. In either case, the molecules of the fluorescer-quencher pair are separate in the absence of immunological reaction.

It is yet another object of the present invention to employ at least two fluorophores, one of which upon excitation exhibits an emission spectrum capable of exciting the second fluorophore which in turn exhibits an emission spectrum measurably detectable and distinguishable from the first emission spectrum and where one of the fluorophores is a phycobiliprotein.

It is still another object of the present invention to simplify the label technology by providing a label having the individual members of a fluorescent energy transfer pair permanently coupled together and where one of the members is a phycobiliprotein.

Recognizing the problems associated with spectrally close excitation and emission spectra of fluorescent energy transfer pairs, additional ways were sought to increase the spectral difference or Stokes shift between the emission and excitation frequencies in order to increase sensitivity of detection. Glazer and Stryer in Biophysics Journal 43:383 (1983) described the covalent linkage of two phycobiliproteins, namely phycoerythrin and allophycocyanine in order to effect fluorescence energy transfer therebetween. Thus, emission at one frequency resulted in energy transfer and excitation at a larger frequency thereby obtaining a significant Stokes shift.

The Glazer et al. system, however, resulted in a protein-to-protein coupling ratio of about one-to-one of the conjugate thereby yielding little or no increase in efficiency to accompany the useful Stokes shift. Further, phycobiliproteins tend to be large molecules (on the order of $10^5$ daltons) and by linking two such large molecules together, an exceedingly large molecule is derived, one which becomes very difficult to employ in a practical manner in various immunoassay applications. The resultant label is so large as to effectively sterically hinder the immunological components, metaphorically describable as the tail wagging the dog.

Consequently, it is still yet another object of the present invention to provide a phycobiliprotein based label having a greater efficiency coupled with a large Stokes shift but not employing multiple phycobiliproteins.

It is yet still another related object to employ fluorescent energy transfer mechanisms to obtain the aforementioned efficiency increase and Stokes shift but to avoid the disadvantages of Glazer and Stryer entailed with one-to-one protein-to-protein coupling ratios.

BRIEF SUMMARY OF THE INVENTION

In accordance with the principles and objects of the present invention, there are provided fluorescent labels useful for immunoassay applications which employ a fluorescent energy transfer mechanism to increase the fluorescent emission efficiency of a phycobiliprotein. This is advantageously accomplished by covalently linking at least one, and in the most preferred embodiment, a plurality of organic dye molecules to the phycobiliprotein in such a manner as to permit energy transfer mechanisms to operate.

Thus, illumination of the label, ideally at the excitation frequency of the organic dye molecule spectral frequency, results in the transfer of at least some of that energy via energy transfer mechanisms to the phycobiliprotein thereby effecting a Stokes shift between the original excitation frequency and the phycobiliprotein emission frequency. The presence of a plurality of the, preferably small molecular weight, organic dye molecules increases the fluorescent efficiency of the phycobiliprotein as compared to the phycobiliprotein by itself.

In the most preferred embodiment of the present invention, the fluorescent label will comprise a plurality of Azure A organic dye molecules covalently coupled to Allophycocyanin.

DETAILED DESCRIPTION AND BEST MODE

In accordance with the desire to decrease the nonspecific noise component in detected fluorescent signals, the present invention employs a phycobiliprotein acceptor molecule which emits in the far red or near infrared region of the spectrum where nonspecific fluorescent noise components naturally diminish. In order to optimize and enhance sensitivity, the present invention also provides a label which comprises the phycobiliprotein in association with accessory molecules suitable for effecting a large Stokes shift via energy transfer mechanisms. Thus, the reduced spectral overlap between the excitation frequencies and the emission frequencies enhances the convenient spectral elimination of excitation frequencies by spectral filters during the detection of emission frequencies.

It has been discovered by the inventors hereof, that such a Stokes shift can be accomplished with phycobiliproteins by coupling them, not with another phycobiliprotein as in the Glazer et al. publication, but with preferably small, low molecular weight organic molecules. Due to the relatively large size of the phycobiliprotein molecule, a plurality of the small organic dyes is preferably attached thereto, each of which can contribute, via fluorescent energy mechanisms, energy to the phycobiliprotein thereby augmenting fluorescent efficiency. As may be expected, higher fluorescent efficiency permits detection at lower label concentrations and thus higher sensitivity.

The small organic molecules preferably have a molecular weight in the range of about 100 to 1000 daltons thereby allowing the attachment of numerous such molecules to the phycobiliprotein without unnecessarily increasing the size or the weight of the resultant label. In order to further enhance the effectiveness of the fluorescent energy transfer mechanism, the preferred label will have the organic dye molecules covalently coupled to the phycobiliprotein, ideally in such a manner as to optimize the energy transfer by carefully regulating the distance therebetween in accordance with the considerations set forth by Stryer in the spectroscopic Ruler article supra.

The resultant label may be employed in a great variety of immunoassays, there remaining merely the step of coupling the label to the appropriate reagent such as the ligand or ligand receptor as desired depending on the component to be tested and the type of assay (competitive, noncompetitive, etc.) to be practiced. The actual coupling techniques have been described in the Oi et al. article or other types of common, well-known coupling techniques may be employed. Additional instruction may be had by reference to the accompanying Examples.

As will be readily appreciated, the organic dye molecules are preferably chosen to provide an excitation frequency spectrum which closely matches the most desirable or available illumination sources. Further, the choice must also take in to account the emission spectra which is preferably closely matched, i.e. preferably less than 5 nm difference, to the excitation spectra of the chosen phycobiliprotein in order to maximize energy transfer therebetween.

Perhaps one of the most reliable and economical high intensity illumination sources is the Helium-Neon (He-Ne) laser. Accordingly, the most preferred embodiment of the label of the instant invention employs Azure A, a small molecular weight organic dye, covalently coupled to the phycobiliprotein Allophycocyanin. Azure A has an excitation frequency of approximately 632 nm and thus closely matches the spectral emission of the He-Ne laser which emits at approximately 632.8 nm. Further, Azure A's emission peak at 645 nm, closely corresponds to the excitation peak of Allophycocyanin. Detection conveniently is accomplished by detecting via a suitably filtered photomultiplier tube or other light sensitive device Allophycocyanin's emission which peaks at 655 nm. Thus, there is a large Stokes shift of approximately 23 nm between the original excitation frequency and the final emission frequency.

Further understanding of the principles and methods of the present invention may be had by reference to the following Examples which are provided by way of illustration and are not intended to be limiting.

EXAMPLE 1

Synthesis and Solid Phase Immobilization of the Allophycocyanin-Azure A Label

Allophycocyanin (from Applied Biosystems, CA) was obtained in a 65% Ammonium Sulfate suspension at a concentration of approximately 5 mg/ml. 0.5 to 5.0 mg of this suspension was dialyzed against 1 liter of 10 mM phosphate buffer Aldrich) overnight at 4° C. in the dark. The dialyzed allophycocyanin was then activated by adding 1.0 to 5.0 mg of 1-Ethyl-3-(3-Dimethylaminopropyl) Carbodiimide-HCl salt (Sigma) and mixed for 1 hour at room temperature. Next, 10 to 100 ug of azure A (Aldrich Chemicals) in 10 to 100 ul of 10 mM phosphate buffer was added to the activated allophycocyanin and the resultant mixture allowed to react overnight at 4° C. in the dark. Upon completion of the reaction, the allophycocyanin-azure A label was purified by repeated concentration and resuspension using a Centricon concentration apparatus (Amicon). The allophycocyanin-azure A conjugated dye was then coupled through the allophycocyanin amino groups to carboxylate derivitized monodisperse 1 to 6 um latex beads (Polysciences) by the standard carbodiimide method. The resulting dye coupled beads were washed and stored in 50 mM Borate Saline Buffer pH 8.5 with 0.1% Sodium Azide (Fisher) added as a preservative. This immobilization method was also performed, albeit with suitable and obvious alterations, for the production of azure A latex beads and allophycocyanin latex beads.

EXAMPLE 2

Fluorescent Measurements

Fluorescent measurements of the unlabeled bead, the azure A bead, the allophycocyanin bead, and the azure A-allophycocyanin labeled bead, were made with a Spectrum III ™ flow cytometer (available from the assignee hereof). The observed results are summarized in the following table:

| Sample | Mean Fluorescence |
|---|---|
| Unlabeled bead | 1.0 |
| Azure A bead | 3.7 |
| Allophycocyanin bead | 29.4 |
| Azure A/Allophycocyanin bead | 439.8 |

As will be readily appreciated, the label of the instant invention, namely the Azure A covalently coupled to the Allophycocyanin, provides a significant increase in the fluorescence signal over any of the individual components. In accordance with the principles and objects of the present invention, it is believed that this is primarily the result of: superior matching of excitation frequency of the label with the preferred helium neon laser light source coupled with the larger Stokes shift thereby increasing filter discrimination efficiency between excitation and emission frequencies, high energy transfer efficiency, and the greater dye-to-protein coupling ratio. Further, it will be understood the principles of the instant invention are not limited to the foregoing, but can be applied to any illuminescence energy transfer process including, for example, chemiluminescence, phosphorescence and thermoluminescence.

What is claimed is:

1. In a method for the detection of a ligand by detecting an immunological reaction between said ligand and a ligand binding receptor specific therefor, the improvement comprising detecting said immunological reaction by detecting a label associated with one of said ligand or ligand binding receptor components, said label comprising a plurality of Azure A molecules covalently coupled to Allophycocyanin under conditions allowing energy transfer therebetween; said detecting further comprising illuminating said label at a first frequency capable of exciting the Azure A molecules and detecting fluorescent emission from said Allophycocyanin at a second frequency.

2. A fluorescent label comprising a plurality of Azure A molecules covalently coupled to Allophycocyanin whereby excitation of said Azure A molecules results in energy transfer to said Allophycocyanin resulting in detectable fluorescent emission by said Allophycocyanin.

* * * * *